(12) United States Patent
Trumble

(10) Patent No.: US 8,075,471 B2
(45) Date of Patent: Dec. 13, 2011

(54) APICAL TORSION DEVICE FOR CARDIAC ASSIST

(75) Inventor: Dennis R. Trumble, Pittsburgh, PA (US)

(73) Assignee: Allegheny-Singer Research Institute, Pittsburgh, PA (US)

( * ) Notice: Subject to any disclaimer, the term of this patent is extended or adjusted under 35 U.S.C. 154(b) by 401 days.

(21) Appl. No.: 11/486,342

(22) Filed: Jul. 12, 2006

(65) Prior Publication Data

US 2008/0015403 A1   Jan. 17, 2008

(51) Int. Cl.
  *A61M 1/12*   (2006.01)
  *A61N 1/362*  (2006.01)
(52) U.S. Cl. ........................................... 600/16
(58) Field of Classification Search .................. 600/2, 4, 600/5, 6, 7, 9, 18, 19, 35
   See application file for complete search history.

(56) References Cited

U.S. PATENT DOCUMENTS

| | | | | |
|---|---|---|---|---|
| 5,957,977 A * | 9/1999 | Melvin | ........................... | 623/3.1 |
| 6,146,325 A * | 11/2000 | Lewis et al. | ..................... | 600/16 |
| 6,387,042 B1 * | 5/2002 | Herrero | .......................... | 600/37 |
| 2003/0078464 A1 * | 4/2003 | Trumble | .......................... | 600/16 |
| 2004/0015040 A1 * | 1/2004 | Melvin | ........................... | 600/16 |
| 2005/0107661 A1 * | 5/2005 | Lau et al. | ......................... | 600/37 |
| 2005/0250976 A1 * | 11/2005 | Melvin et al. | ................... | 600/16 |
| 2005/0256363 A1 * | 11/2005 | Bolling et al. | .................. | 600/16 |
| 2006/0009676 A1 * | 1/2006 | Melvin | ........................... | 600/37 |
| 2006/0155160 A1 * | 7/2006 | Melvin et al. | ................... | 600/16 |

* cited by examiner

*Primary Examiner* — Carl H Layno
*Assistant Examiner* — Allen Porter, Jr.
(74) *Attorney, Agent, or Firm* — Pepper Hamilton LLP

(57) ABSTRACT

An apparatus for assisting a heart of a patient includes an actuator for wringing blood concurrently from both the right and left ventricles of the heart without contacting circulating blood of the patient. The apparatus includes a power source connected to the actuator to power the actuator. A method for assisting a heart of a patient includes the steps of powering an actuator in contact with the heart with a power source. There is the step of wringing blood concurrently from both the right and left ventricles of the heart without contacting circulating blood of the patient with the actuator.

8 Claims, 2 Drawing Sheets

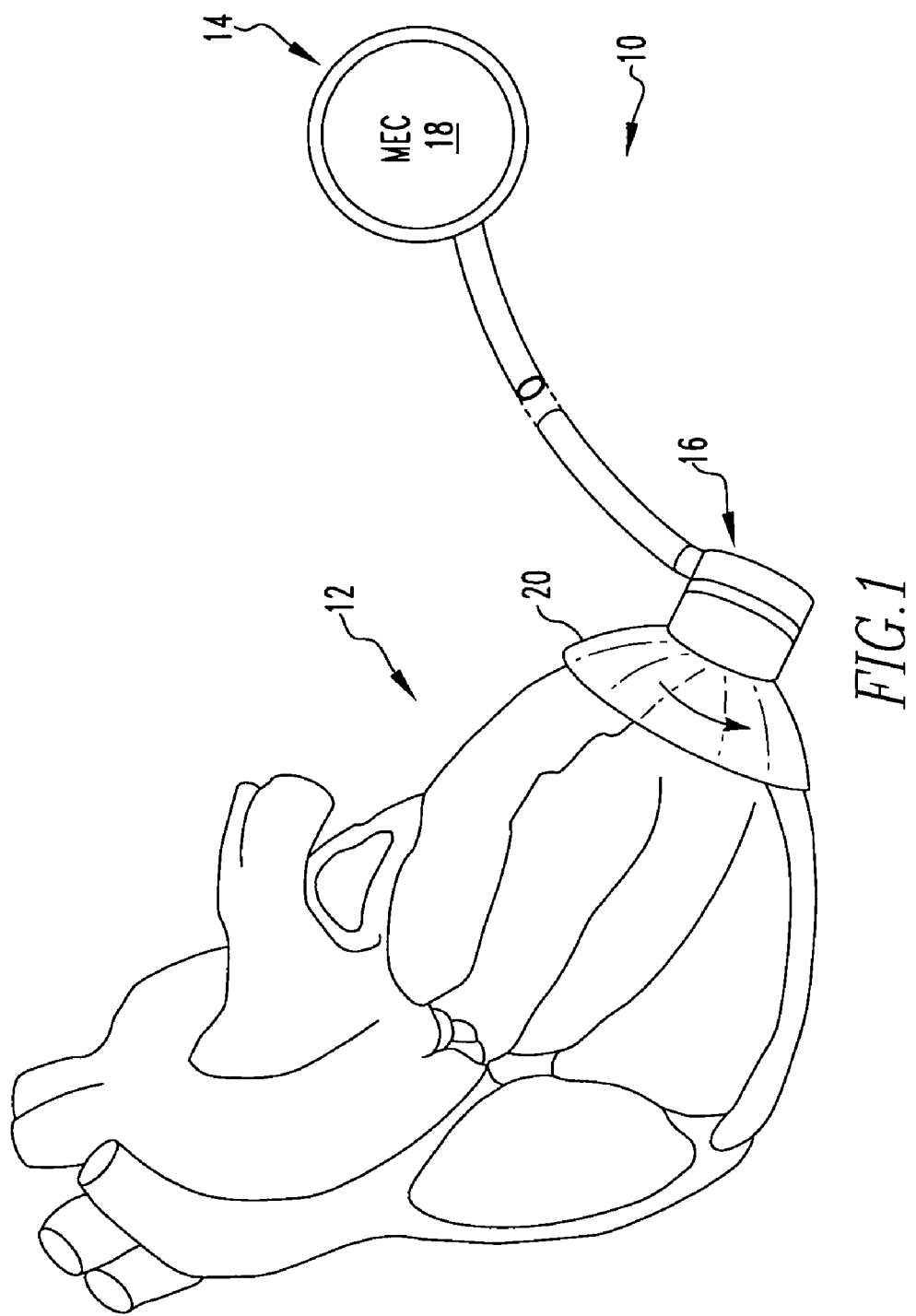

APICAL TORSION DEVICE FOR CARDIAC ASSIST

FIELD OF THE INVENTION

The present invention is related to an apparatus for assisting a heart of a patient by wringing blood from the heart. More specifically, the present invention is related to an apparatus for assisting a heart of a patient by wringing blood concurrently from both the right and left ventricles of the heart without contacting circulating blood of the patient.

BACKGROUND OF THE INVENTION

Congestive heart failure (CHF) is a highly debilitating and progressive illness that afflicts tens of millions of people worldwide. In the United States, over 4.8 million people currently suffer from this condition and it is estimated that CHF will ultimately affect one in every five Americans. With over 400,000 new cases diagnosed each year in the United States alone, CHF is a rapidly growing public health problem that has proven difficult to treat. Current pharmacologic therapies can relieve symptoms in most patients but do not appreciably stem the course of the disease. Indeed, despite optimal pharmacotherapy and outpatient management, median survival times following initial diagnosis are alarmingly brief—just 1.7 years in men and 3.2 years in women. At present, heart transplantation remains the most effective treatment, but a small donor pool and the serious side effects of immunosuppressive drugs limit this approach. Mechanical circulatory support with a left ventricular assist device (VAD) has been shown to reverse the physiologic effects of severe congestive heart failure and improve both survival and quality of life when compared to medical therapy. In short-term use, as in bridge to cardiac transplantation, this approach has been particularly effective. When intended for permanent support, however, VAD technology has been plagued by problems associated with the complexities of extracorporeal power delivery and thrombolic complications associated with artificial blood contacting surfaces. An alternate approach that allows for a biologically-powered form of mechanical circulatory support devoid of blood-contacting surfaces would therefore be a major advance in the treatment of CHF.

The present invention is related to a broad family of commercial cardiac assist devices the vast majority of which draw blood directly from the heart and pump it back to the systemic circulation by mechanical means. This typically involves using either a blood-borne impeller or a compressible blood sac, both of which remain in intimate contact with the blood being pumped. As a consequence, thromboembolic events, the need for anticoagulation, hemolysis, immune reactions and infections all contribute to the morbidity and mortality of patients supported by these devices. Other more experimental devices avoid direct contact with the blood by using the heart itself as the blood sac. These various "cardiac compression" devices (Anstadt cup; CardioSupport system; HeartPatch; AbioBooster) are similar to the disclosed technology only insofar as they seek to improve cardiac output by manipulating the external structures of the heart. Their mechanism of action, however, is significantly different.

As mentioned above, the existing technology is embodied in several experimental devices designed to achieve direct cardiac compression. These various devices are described in the following publications:

Huang Y, Gallagher G, Plekhanov S, Morita S, Brady P W, Hunyor S N. HeartPatch implanted direct cardiac compression: effect on coronary flow and flow patterns in acute heart failure sheep. *ASAIO J.* 2003 May-June; 49(3):309-13.

Oz M C, Artrip J H, Burkhoff D. Direct cardiac compression devices. *J Heart Lung Transplant.* 2000 October; 21(10):1049-55. Review.

Kavarana M N, Helman D N, Williams M R, Barbone A, Sanchez J A, Rose E A, Oz M C, Milbocker M, Kung R T. Circulatory support with a direct cardiac compression device: a less invasive approach with the AbioBooster device. *J Thorac Cardiovasc Surg.* 2001 October; 122 (4):786-7.

Williams M R, Artrip J H. Direct cardiac compression for cardiogenic shock with the CardioSupport system. *Ann Thorac Surg.* 2001 March; 71(3 Suppl):S188-9.

Lowe J E, Anstadt M P, Van Trigt P, Smith P K, Hendry P J, Plunkett M D, Anstadt G L. First successful bridge to cardiac transplantation using direct mechanical ventricular actuation. *Ann Thorac Surg.* 1991 December; 52(6):1237-43; discussion 1243-5.

BRIEF SUMMARY OF THE INVENTION

The present invention has at least one major advantage over other mechanical VADs currently on the market: there are no blood-contacting parts to cause thrombus formation, hemolysis, immune reactions, or blood-borne infections-complications that severely limit the effectiveness of all commercial VAD technologies available today. A second key advantage over present-day blood pumps could potentially be realized by driving the ATD using a muscle-powered pump developed in-house. This would serve to eliminate additional complications associated with the use of percutaneous drivelines and transcutaneous transmission schemes. There are several devices being development elsewhere that, like the ATD, aim to improve cardiac function by manipulating the surface of the heart (see above). However, these technologies generally involve applying pressure directly to the ventricular free walls in order to push them in toward the ventricular septum. The potential injurious effects of direct mechanical compression of the myocardium (e.g., myocardial contusions, increased arrhythmias and myocardial ischemia) are not well known and therefore remain a concern for all such support mechanisms. The ATD, on the other hand, acts to wring blood from the heart with minimal contact with the epicardial surface, thereby minimizing the risk of contact abrasion, coronary compression, and rhythm disruption. Moreover, because the surface of the heart remains free and uncovered, ATDs can be used in conjunction with coronary artery bypass grafts and/or implantable defibrillator pads without risk of interference.

The present invention pertains to an apparatus for assisting a heart of a patient. The apparatus comprises an actuator for wringing blood concurrently from both the right and left ventricles of the heart without contacting circulating blood of the patient. The apparatus comprises a power source connected to the actuator to power the actuator.

The present invention pertains to a method for assisting a heart of a patient. The method comprises the steps of powering an actuator in contact with the heart with a power source. There is the step of wringing blood concurrently from both the right and left ventricles of the heart without contacting circulating blood of the patient with the actuator.

BRIEF DESCRIPTION OF THE SEVERAL VIEWS OF THE DRAWING

In the accompanying drawings, the preferred embodiment of the invention and preferred methods of practicing the invention are illustrated in which:

FIG. 1 is a schematic representation of the apparatus of the present invention.

DETAILED DESCRIPTION OF THE INVENTION

Figure 3:
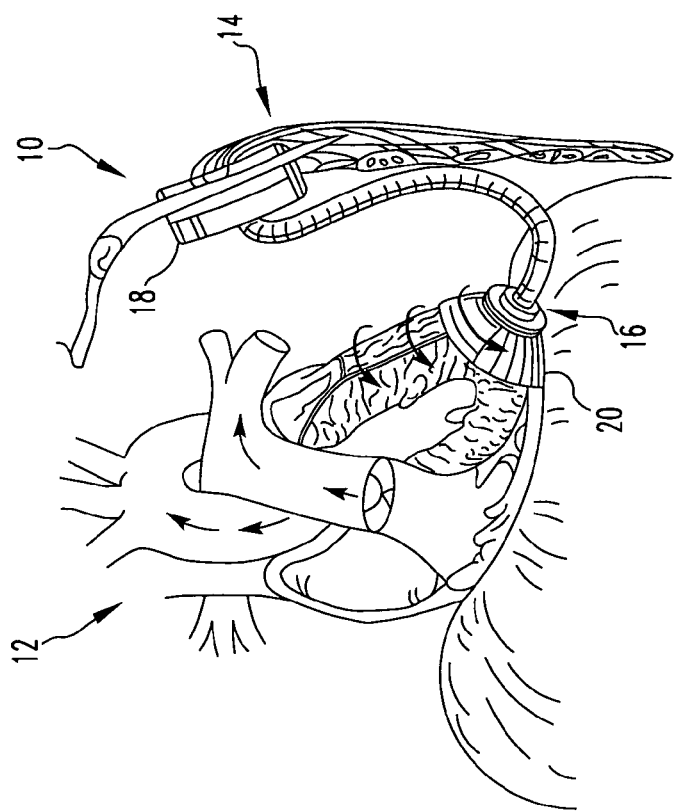
FIG. 3 is a schematic representation of the apparatus in an actuated state.
Figure 2:
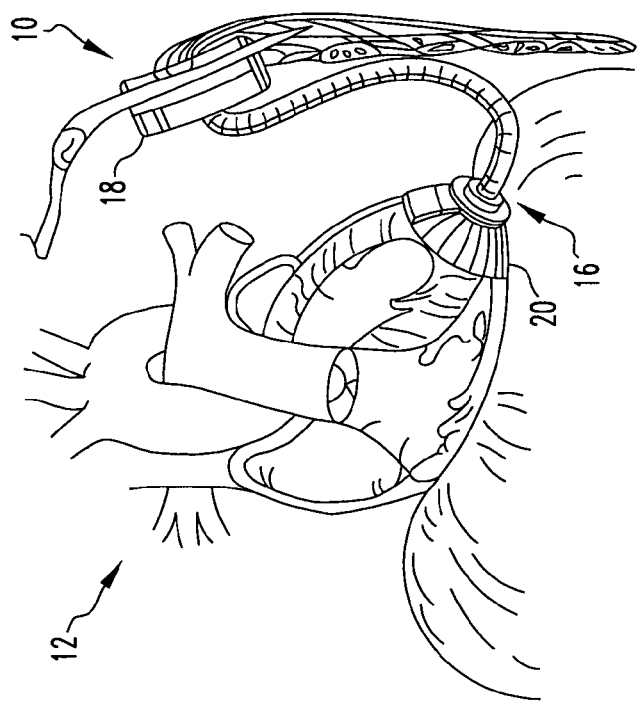
FIG. 2 is a schematic representation of the apparatus in an unactuated state.

Referring now to the drawings wherein like reference numerals refer to similar or identical parts throughout the several views, and more specifically to FIG. 1 thereof, there is shown an apparatus 10 for assisting a heart 12 of a patient. The apparatus 10 comprises an actuator 16 for wringing blood concurrently from both the right and left ventricles of the heart 12 without contacting circulating blood of the patient. The apparatus 10 comprises a power source 14 connected to the actuator 16 to power the actuator 16.

Preferably, the actuator 16 is a rotary actuator adapted to be attached to the apical aspect of the heart 12 so the apex of the heart 12 can be turned counterclockwise, as viewed from the apex, with respect to the base of the heart 12 to apply torsion to restore natural wringing motion to the heart 12. The actuator 16 is preferably adapted to be attached to the epicardial surface of the heart 12 so as not to contact blood.

Preferably, the actuator 16 provides normal apical rotation or supernormal torsion to the heart 12. The actuator 16 preferably coincides with the systolic phase of the cardiac cycle. Preferably, the power source 14 includes an electric, pneumatic, or low-volume hydraulic power source 14. The power source 14 is preferably a muscle energy converter 18.

The present invention pertains to a method for assisting a heart 12 of a patient. The method comprises the steps of powering an actuator 16 in contact with the heart 12 with a power source 14. There is the step of wringing blood concurrently from both the right and left ventricles of the heart 12 without contacting circulating blood of the patient with the actuator 16.

Preferably, the wringing step includes the step of turning the apex of the heart 12 counterclockwise with a rotary actuator 16 attached to the apical aspect of the heart 12, as viewed from the apex, with respect to the base of the heart 12 to apply torsion to restore natural wringing motion to the heart 12. There is preferably the step of coinciding the wringing with the actuator 16 with the systolic phase of the cardiac cycle.

In the operation of the preferred embodiment, the technology described herein, called an Apical Torsion Device (ATD), is designed to enhance the pumping action of a failing heart by effectively 'wringing' blood from both the right and left ventricles concurrently. This is accomplished by attaching a rotary actuator 16 to the apical aspect of the heart 12 so that the apex can be turned counterclockwise (as viewed from the apex) with respect to the base of the heart 12 as shown below. The applied torsion serves to restore the natural wringing motion observed to occur in healthy hearts—a contractile trait that is far less prominent in most diseased hearts. The actuator 16 is placed on the epicardial surface so as not to contact the blood and can be used either to restore normal apical rotation (9-12 degrees) or provide supra-normal torsion (15 degrees or more) to further improve ventricular emptying. Device actuation is to coincide with the systolic phase of the cardiac cycle and will assist ejection directly by mechanical means and indirectly by lowering wall stress (thereby allowing cardiomyocytes to shorten more completely). The actuator 16 can conceivably be powered electrically, pneumatically, or by low-volume hydraulics. The hydraulic version—the preferred embodiment—would allow the device to be used in conjunction with a muscle-powered pump previously developed here at ASRI (see U.S. Pat. No. 6,945,926: Improved Muscle Energy Converter). Combined, these two technologies would form a totally self-contained circulatory support system devoid of blood contacting surfaces and external power sources.

The preferred embodiment of how the actuator itself is to be anchored in this case is to fix the actuator directly to the sternum or to the ribs closest to the cardiac apex (ribs 5 and 6 in most people) using a mechanical screw-and-plate type clamping means used most commonly in surgical orthopedic applications (e.g., U.S. Pat. Nos. 7,048,739 and 5,752,958, incorporated by reference herein).

Connection to the heart will be made using a circular cup-shaped device placed over the cardiac apex so that the sides of the cup 20 extend about 2-3 cm up from the apical tip. Fixation may be made in one of several ways: 1) two or more heavy-gauge needles can be pushed across the diameter of the cup (through the apex) and secured on opposite sides to "skewer" the device into place; 2) the device can be fitted with numerous barbs to secure the epicardium to the inner surface of the cup; 3) the cup can be made with an array of holes through which numerous sutures can be passed and subsequently used to sew the apex to the cup; and 4) the inner surface of the cup can be made rough to encourage fixation via collagen ingrowth (to be used in combination with one of the aforementioned fixation methods).

The rotary actuator will be positioned beneath the fixation cup and connected directly to it by a short metallic shaft. The shaft will rotate in response to fluid entering the actuator housing, preferably from the MEC. (The MEC will be connected to the actuator via a simple hydraulic tube.) There are a number of ways to create a hydraulic rotary actuator. One is to use an expandable bellows to push the shaft through a spiral groove in a manner analogous to a helical sliding spline. Another would be to use a simple rack-and-pinion mechanism. A third would be to employ a Scotch-yoke arrangement. While these three mechanisms do not constitute an exhaustive list by any means, they are certainly among but these are certainly the most common techniques used to effect rotary movement by hydraulic means.

The following patents, all of which are incorporated by reference herein, describe the respective type of embodiments described above.

Helical Spline:

U.S. Pat. No. 5,241,895—Air-powered splined rotary actuator

U.S. Pat. No. 4,745,847—Helical splined rotary actuator

U.S. Pat. No. 4,422,366—Rotary helical actuator

Rack & Pinion:

U.S. Pat. No. 6,684,727—Rack and pinion steering apparatus

U.S. Pat. No. 6,363,833—Piston for hydraulic power assist rack and pinion steering system U.S. Pat. No. 6,138,789—Hydraulic rack and pinion steering Scotch Yoke:

U.S. Pat. No. 5,078,017—Motion translation device of scotch yoke type

U.S. Pat. No. 4,272,996—Scotch yoke having a curved track

U.S. Pat. No. 4,056,011—Scotch yoke

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

The invention claimed is:

1. An apparatus for assisting a heart of a patient comprising:
   rotary actuator for wringing blood concurrently from both the right and left ventricles of the heart without contacting circulating blood of the patient, wherein the rotary actuator is adapted to be attached to the epicardial surface of the apex of the heart so as not to contact blood and the rotary actuator is configured to turn the apex of the heart counterclockwise with respect to the base of the heart in order to apply torsion to restore natural wringing motion to the heart; and
   the rotary actuator includes a cup-shaped device adapted to be placed over and attached to the apex of the heart and is further adapted to extend about 2-3 cm up from the heart's apical tip, wherein the cup-shaped device has an array of holes through which sutures are configured to pass; and
   a power source connected to the rotary actuator to power the actuator.

2. An apparatus as described in claim 1, wherein the rotary actuator is further configured to provides normal apical rotation or supernormal torsion to the heart.

3. An apparatus as described in claim 2 wherein the rotary actuator is configured to turn the apex of the heart counterclockwise with respect to the base of the heart during the systolic phase of the cardiac cycle.

4. An apparatus as described in claim 3 wherein the power source includes an electric, pneumatic, or hydraulic power source.

5. An apparatus as described in claim 4 wherein the power source is a muscle energy converter.

6. An apparatus as described in claim 1 wherein the cup-shaped device has an inner surface which is rough.

7. A method for assisting a heart of a patient comprising the steps of:
   powering an actuator in contact with the heart with a power source; and
   wringing blood concurrently from both the right and left ventricles of the heart without contacting circulating blood of the patient, the actuator includes a cup-shaped device placed over and attached to the cardiac apex which extends about 2-3 cm up from the heart's apical tip, the wringing step includes the step of turning the apex of the heart counterclockwise with a rotary actuator attached to the apex of the heart through the cup-shaped device, as viewed from the apex, with respect to the base of the heart to apply torsion to restore natural wringing motion to the heart, the cup-shaped device has an array of holes through which sutures pass to attach the cup-shaped device to the heart.

8. A method as described in claim 7 including the step of coinciding the wringing with the actuator with the systolic phase of the cardiac cycle.

* * * * *